United States Patent

Peschke

[11] Patent Number: 5,135,493
[45] Date of Patent: Aug. 4, 1992

[54] STRIP CARTRIDGE ADAPTER AND STRIP CARTRIDGE FOR IMPLANT DEVICE

[75] Inventor: Mark Peschke, Clinton, Ind.

[73] Assignee: Pitman-Moore, Inc., Lake Forest, Ill.

[21] Appl. No.: 581,612

[22] Filed: Sep. 10, 1990

[51] Int. Cl.$^5$ .............................................. A61M 5/00
[52] U.S. Cl. ...................................... 604/61; 604/57; 604/59; 604/60; 604/62
[58] Field of Search .................. 604/59, 60, 61, 62, 604/63, 64, 57, 130; 221/68-72, 74, 75, 79, 80, 312 B

[56] References Cited

U.S. PATENT DOCUMENTS

| | | |
|---|---|---|
| 1,347,622 | 7/1920 | Deininger . |
| 2,502,909 | 4/1950 | Wick et al. . |
| 2,601,852 | 7/1952 | Wendt . |
| 2,620,796 | 12/1952 | Eriksen et al. . |
| 2,632,444 | 3/1953 | Kas . |
| 2,761,446 | 3/1955 | Reed . |
| 2,850,013 | 9/1958 | Cardis . |
| 3,402,712 | 9/1968 | Eisenhand . |
| 3,520,299 | 7/1970 | Lott . |
| 3,744,493 | 7/1973 | Booher et al. . |
| 3,774,607 | 11/1973 | Schmitz ............................ 604/61 |
| 4,077,406 | 3/1978 | Sandhage et al. .................. 604/61 |
| 4,105,030 | 8/1978 | Kersco . |
| 4,154,239 | 5/1979 | Turley . |
| 4,223,674 | 9/1980 | Fluent et al. . |
| 4,400,170 | 8/1983 | McNaughton et al. . |
| 4,403,610 | 9/1983 | Lodge et al. ........................ 604/61 |
| 4,447,223 | 5/1984 | Kaye et al. ......................... 604/61 |
| 4,451,254 | 5/1984 | Dinius et al. . |
| 4,474,572 | 10/1984 | McNaughton et al. ............ 604/61 |
| 4,518,384 | 5/1985 | Tarello et al. . |
| 4,531,938 | 7/1985 | Kaye et al. . |
| 4,576,591 | 3/1986 | Kaye et al. ......................... 604/61 |
| 4,597,753 | 7/1986 | Turley . |
| 4,673,387 | 6/1987 | Phillips et al. ..................... 604/62 |
| 4,687,465 | 8/1987 | Prindle et al. ..................... 604/62 |
| 4,762,515 | 8/1988 | Grimm .............................. 604/61 |
| 4,787,384 | 11/1988 | Campbell et al. . |
| 4,799,921 | 1/1989 | Johnson et al. . |
| 4,846,793 | 7/1989 | Leonard et al. . |
| 4,976,686 | 12/1990 | Ball et al. ........................... 604/61 |

Primary Examiner—Stephen C. Pellegrino
Assistant Examiner—Glenn K. Dawson
Attorney, Agent, or Firm—Wendell Ray Guffey; Thomas L. Farquer; Lance G. Johnson

[57] ABSTRACT

A strip carriage adapter and corresponding strip cartridge which allows conversion of a handgun-type implanter which uses cylinder-type pellet cartridges to one which uses strip-type pellet cartridges.

4 Claims, 6 Drawing Sheets

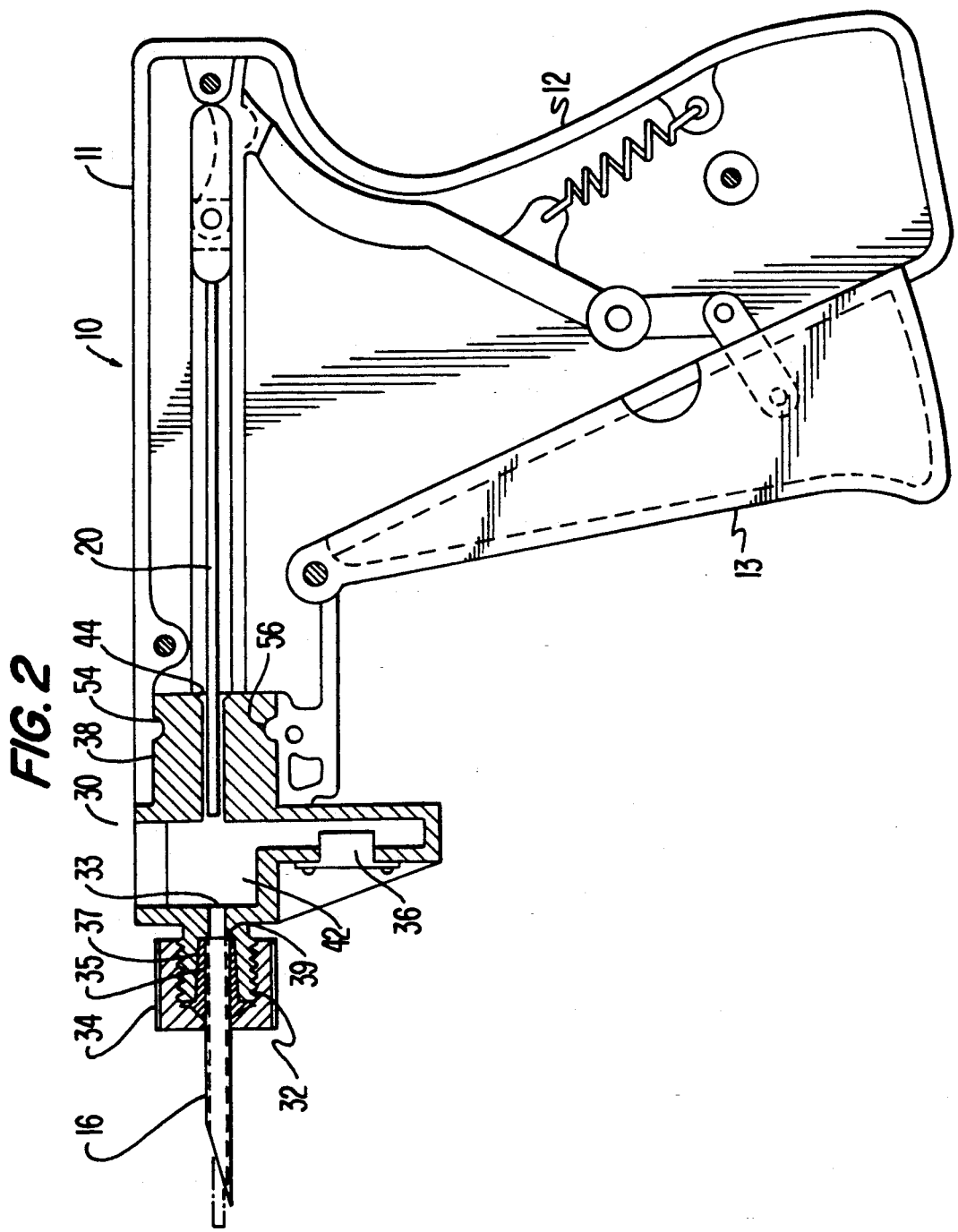

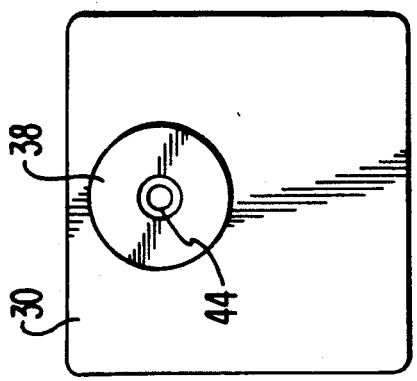
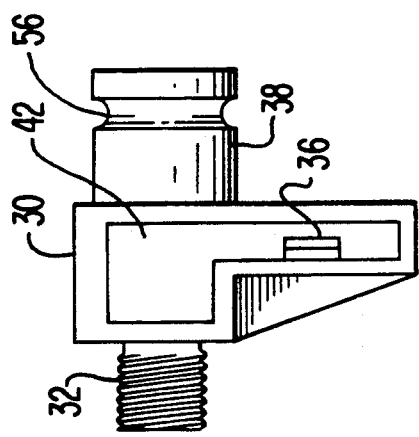
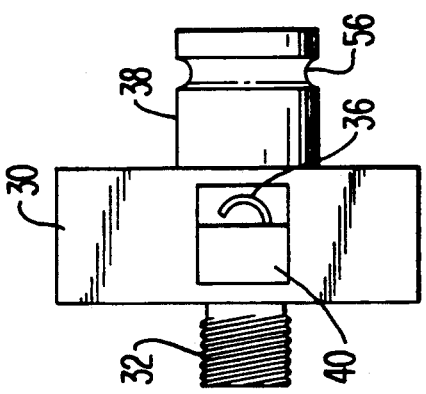
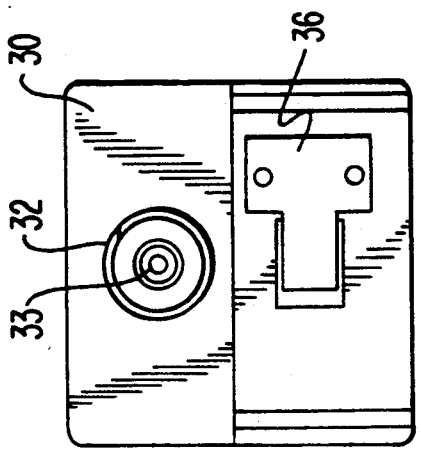

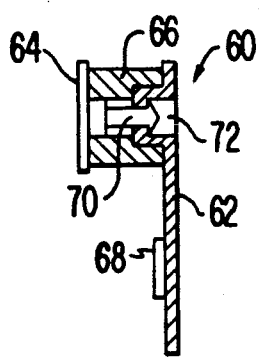
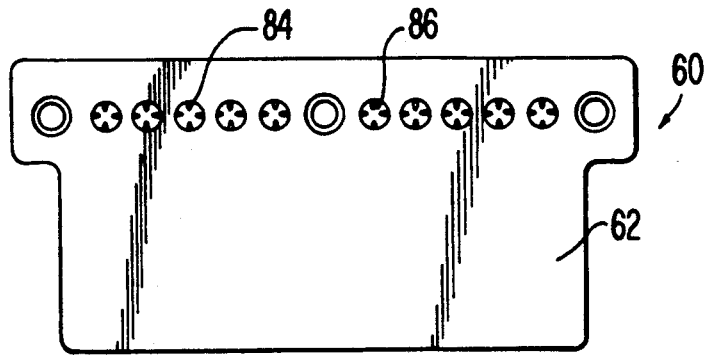
FIG.4A  FIG.4B
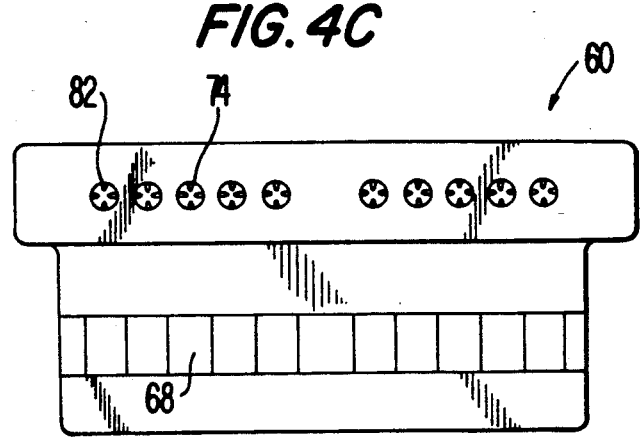
FIG.4C
FIG.5A
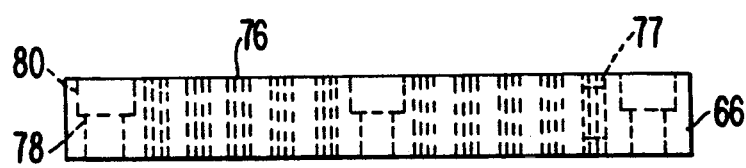
FIG.5B
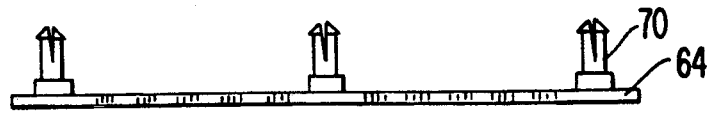
FIG.5C

STRIP CARTRIDGE ADAPTER AND STRIP CARTRIDGE FOR IMPLANT DEVICE

TECHNICAL FIELD

The present invention relates to devices for the implanting of anabolic or other medicinal pellets under the skin of domestic animals.

BACKGROUND OF THE INVENTION

It is often desirable with domestic animals (e.g. cattle, swine, chickens) to implant into the animals a solid or semi-solid medicament. Such practice is common, for example, for growth stimulation of cattle and swine. Typically, growth stimulating hormones are implanted in the neck or ear of the animal, to remain there for an extended period of time. Because the ear is a throwaway organ, it is a preferred implantation site. Any implate residue present in the ear at slaughter will not enter channels of commerce to become ingested by humans or domestic animals.

A typical medicament implanter device comprises a hand-held instrument built of a size consistent with the size of the animal (large for cattle, small for chickens). The body of the instrument is typically shaped either like a handgun, or alternatively, like a large hypodermic syringe with a receive-dispenser for the medicament implant. Both types use an apertured needle to make a sizable non-coring puncture opening into the skin (e.g. of the ear) of the animal and form a cavity in the skin occupied temporarily by the needle of the instrument.

U.S. Pat. Nos. 4,531,938 issued to Kay et al., 4,451,254 issued to Dinius et al., and 2,761,446 issued to Reed are representative of syringe type implanters. U.S. Pat. Nos. 3,774,607 issued to Schmitz, 4,576,591 issued to Kay et al., 4,447,223 issued to Kay et al., and 4,400,170 issued to McNaughton et al. are representative of handgun type implanters.

In a common handgun-type implanter such as that describe in U.S. Pat. No. 3,774,607 ('607 patent), which is herein incorporated by reference, the medicament implants are purchased already loaded into a cartridge. That is, the cartridge is purchased fully loaded and is disposed of when all of the implants have been used. Unfortunately, with such cartridges the framer is forced to purchase a minimum number of implants (the cartridge in the illustrated model of the '607 patent contains 24 pellets), which may be considerably more than he wishes to purchase. Furthermore, the handgun-type implanter of the '607 patent only allows use of circular, cylinder-type cartridges. Therefore, farmers who might prefer strip cartridges, have no choice but to use the standard cylinder-type cartridge with its relatively large number of doses.

SUMMARY OF THE INVENTION

Accordingly, it is an object of the invention to provide a cartridge which holds significantly fewer doses then the standard cylinder-type cartridge.

It is another object of the invention to provide a strip-type cartridge.

It is further object of the invention to provide an adapter such that the '607 type implant gun can be converted to allow use of such strip-type cartridges.

It is a still further object of the invention to design the adapter such that the handgun-type implanter can readily be converted back to allow use of cylinder-type cartridges.

The present invention contemplates a pellet implant gun which receives cylinder-type pellet cartridges in combination with an adapter which allows operation of the gun with strip-type pellet cartridges. Strip cartridges are provided with contain any desired number of pellet dosages. The number of dosages per strip cartridge can be varied practically infinitely by simply increasing or decreasing the length of the strip cartridge.

Various advantages and features of novelty which characterize the invention are pointed out with particularity in the claims annexed thereto and forming a part hereof. However, for a better understanding of the invention, its advantages, and objects obtained by its use, reference should be had to the drawings which form a further part hereof, and to the accompanying descriptive matter, in which there is illustrated and described preferred embodiments of the invention.

BRIEF DESCRIPTION OF THE DRAWINGS

FIG. 2 is a side perspective of a pellet implant gun with a strip cartridge adapter in place according to the present invention.

FIGS. 3A, 3B, 3C, and 3D are front, back, side and top views respectively of the strip cartridge adapter shown in FIG. 2.

FIGS. 4A, 4B, and 4C are side, rear and front views respectively of a strip cartridge according to the present invention.

FIGS. 5A, 5B, and 5C represent respectively top views of the back piece, the middle or magazine piece and the front piece of the strip cartridge shown in FIGS. 4A, 4B and 4C.

DETAILED DESCRIPTION OF THE INVENTION

Figure 1:
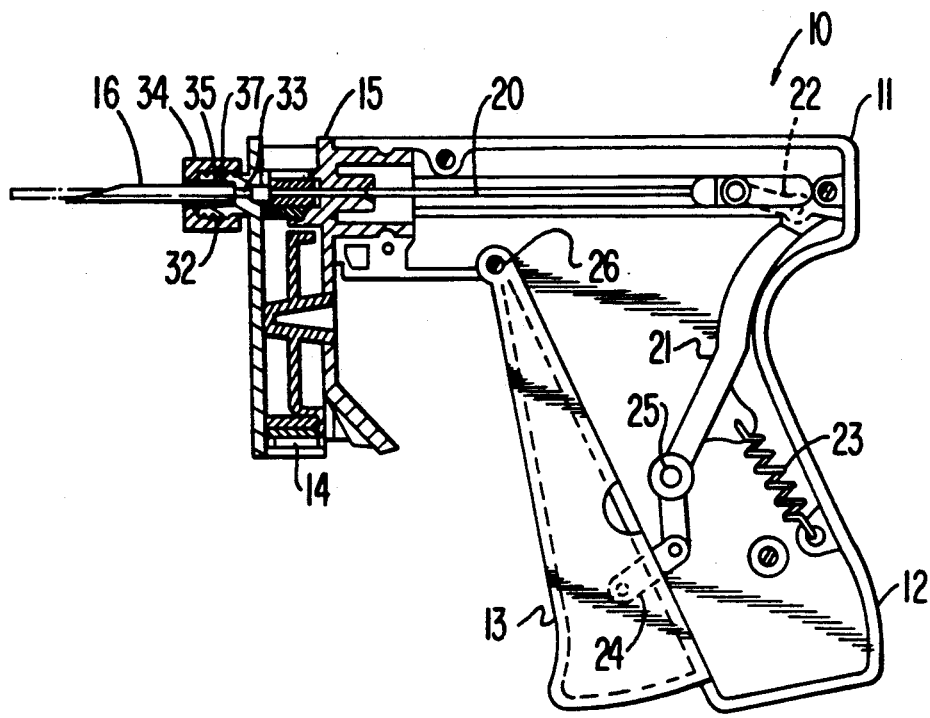
FIG. 1 is a side perspective of a prior art pellet implant gun with a cylinder-type cartridge.

Referring now to the drawings in which like numerals denote similar elements, and more particularly to FIG. 1, there is shown by way of illustration, but not of limitation, a prior art cartridge implant gun 10 according to U.S. Pat. No. 3,774,607, which is herein incorporated by reference, with a body portion 11, a grip portion 12, a trigger member 13, a standard cylinder-type pellet cartridge 14, a standard cartridge holder 15, and a needle 16.

Within the body 11 is a plunger 20, which in its withdrawn position is wholly within the body 11 and in its extended position extends the length of the needle 16. The plunger 20 is controlled by operating lever 21 and plunger link 22. The operating lever is restrained by biasing spring 23 and is controlled by trigger link 24 connected to the trigger portion 13 which rotates around trigger pivot 26 causing the operating lever 21 to rotate about lever pivot 25 thus controlling the position of plunger 20. The structure and operation of these mechanisms will not be further described as this portion of the implant gun in conventional.

Figure 2A:
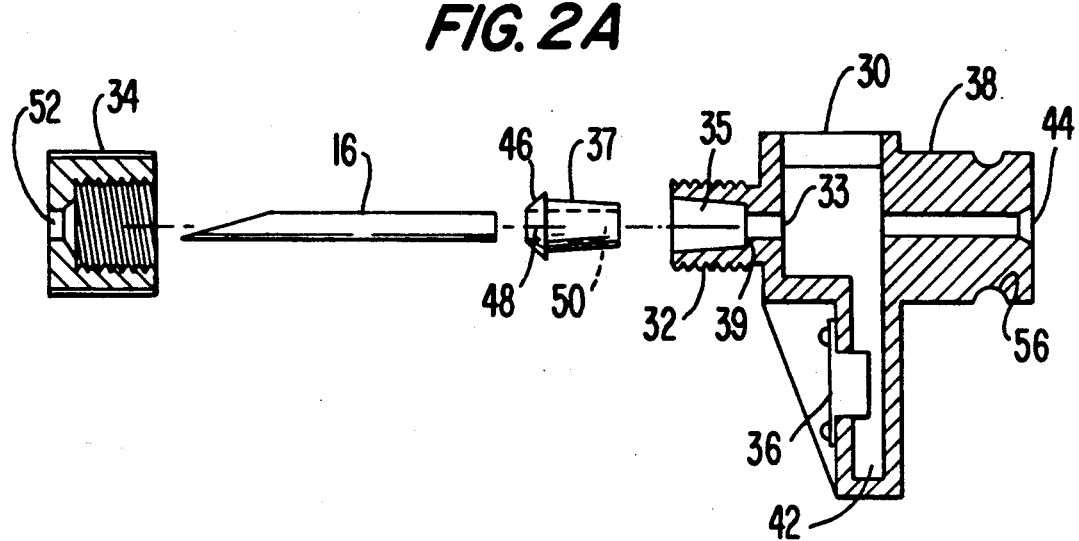
FIG. 2A is an exploded view of the strip cartridge adapter/needle assembly according to the present invention.
Figure 6A:
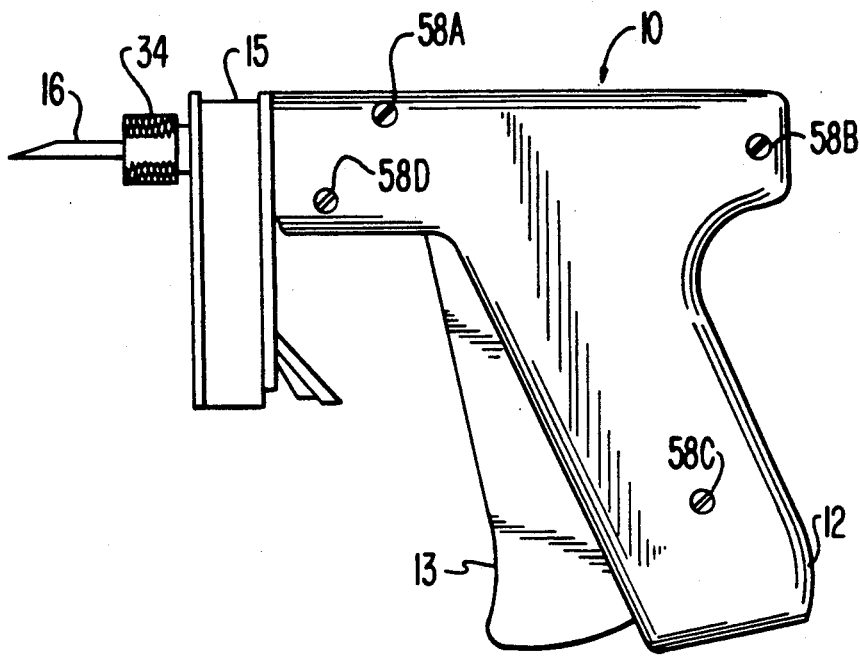
FIGS. 6A, 6B, 6C and 6D display the step-wise procedure of replacing a standard cylinder type cartridge holder with the strip cartridge adapter shown in FIG. 2.
Figure 6B:
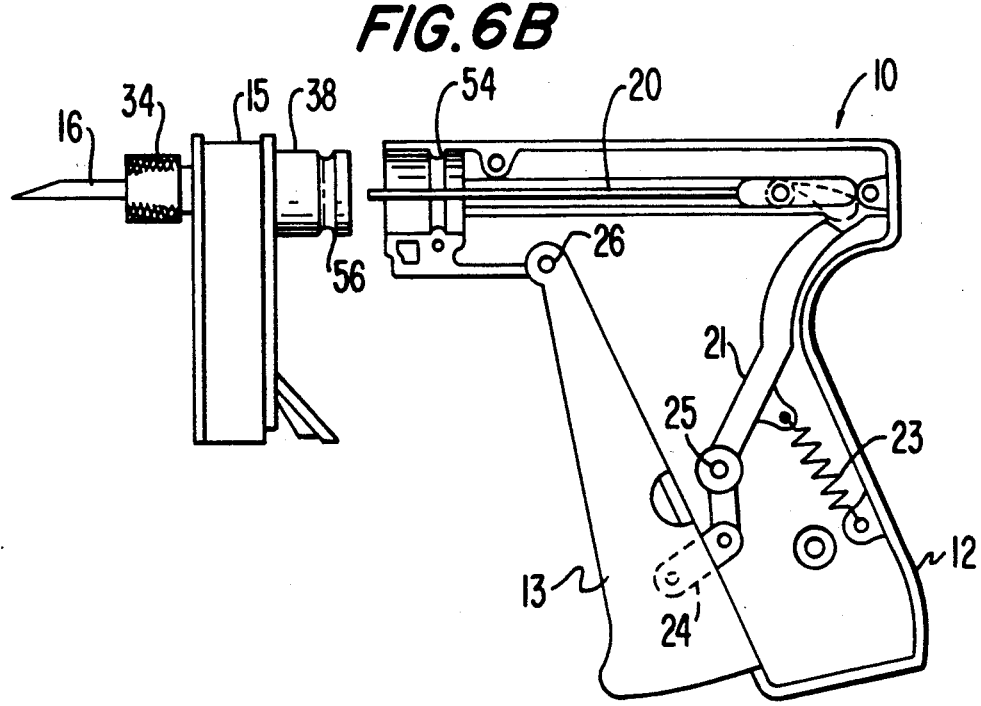
Figure 6C:
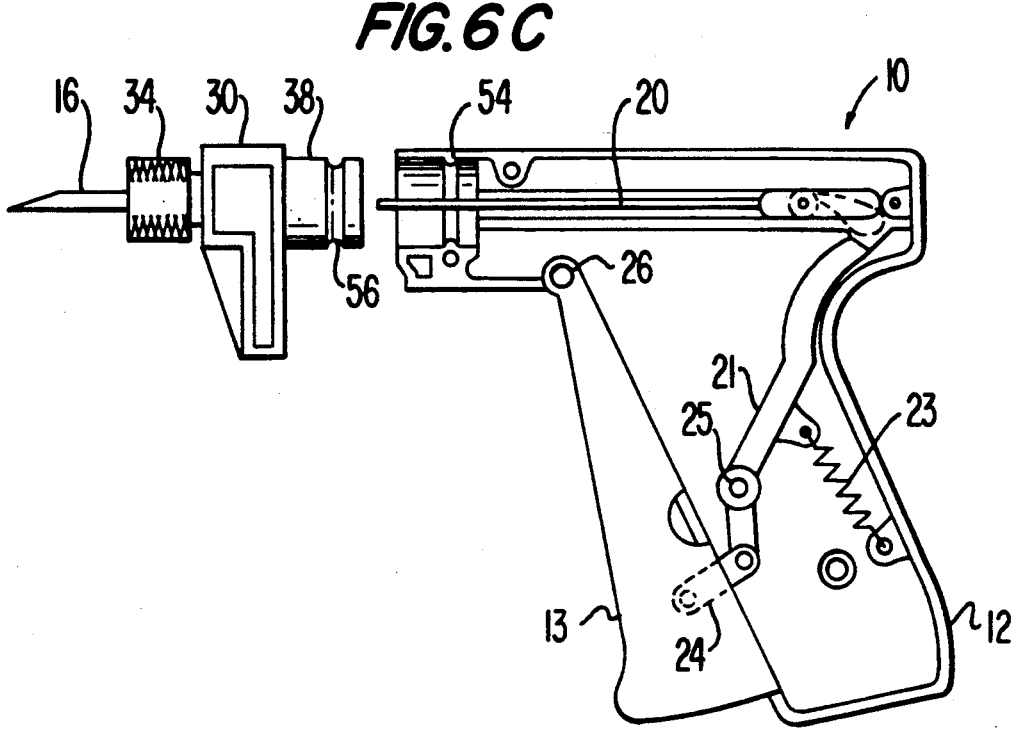
Figure 6D:
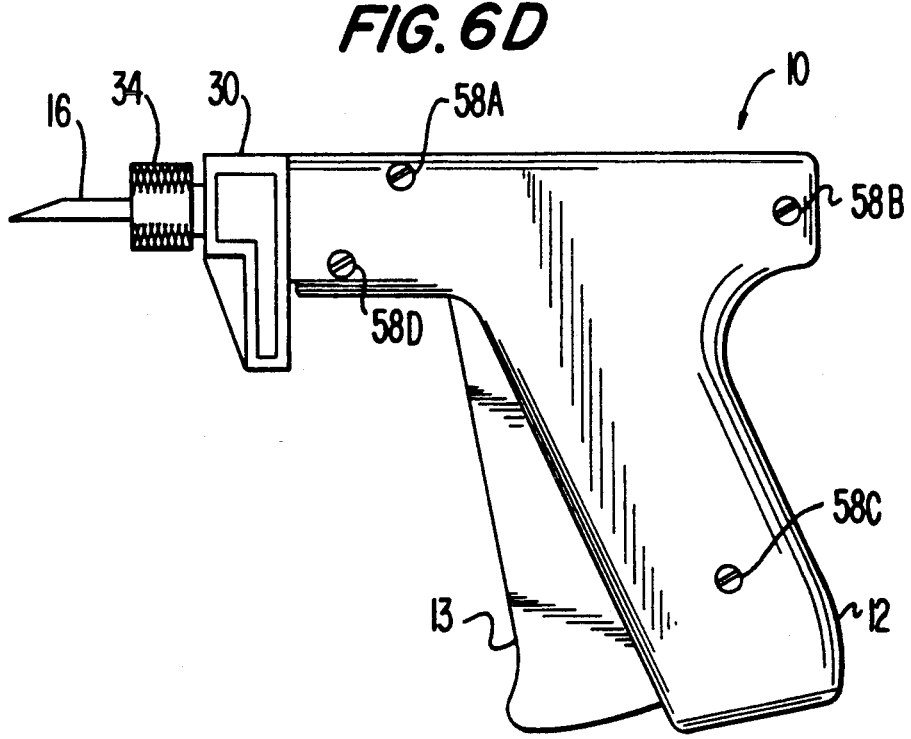

FIG. 2 displays the same cartridge implant gun 10 with an L-shaped strip cartridge adapter 30 according to the present invention in place of the standard cartridge holder 15. The strip cartridge adapter 30 includes a threaded knob 32 having a bore or pellet conveying conduit 33 axially aligned with the line of travel of the plunger 20. FIG. 2A provides an exploded view of the adapter/needle assembly. Threaded knob 32 contains a bore 35, which is somewhat larger in diameter than, and axially aligned with, bore 33. A shoulder 39 is formed at the point where bores 35 and 33 meet. Collet 37, which slidably fits into bore 35 until it abuts shoulder 39, has a conical end 46 with compression slits 48 and a bore 50. Hollow needle 16 slidably fits into collet 37 until it also abuts shoulder 39. The inside diameter of hollow needle 16 is approximately equal to or slightly larger than bore 33 allowing easy passage of plunger 20 through bore 33 and into and through hollow needle 16. Threaded cap 34, which threadedly engages the threaded knob 32, has a hole 52 which fits over needle 16. When threaded cap 34 is tightened onto threaded knob 32, it applies compressive force on collet 37, which thereby forcibly grips hollow needle 16 preventing lateral or radial movement thereof.

The strip cartridge adapter 30 also includes an L-shaped cartridge receiving cavity 42 and a convenient means for mounting the strip cartridge adapter 30 to body portion 11. An example of such a mounting means is a mounting cylinder 38 which may fit within the skin portion of body portion 11 and be attached by any convenient means. An example of such attachment means includes a rib ring 54 within the skin portion of the body portion 11 which mates with the detent or notch ring 56 about the outer surface of the mounting cylinder 38. The mounting means such as mounting cylinder 38 may also contain a plunger guide 44 to hold the forward end of the plunger 20 in its withdrawn position and to guide the plunger 20 during its extension through the needle 16.

The strip cartridge adapter may also contain a positioning detent spring 36 for holding and positioning an L-shaped strip cartridge 60 of FIGS. 4A-4C within the cartridge receiving cavity 42. Additionally, as shown in FIG. 3D, a view port 40 may be provided on the top portion of the strip cartridge adapter 30, allowing the operator to visually assure proper indexing of a pellet dose 77.

A preferred embodiment of the strip cartridge 60 is displayed in FIGS. 4A, 4B, 4C, 5A, 5B, and 5C. The strip cartridge 60 is preferably made of three pieces of molded plastic: a front plate 64, a magazine 66, and a rear plate 62.

The front plate 64 includes apertures 82 which correspond to the magazine cylinders 76 to be described. Each of the apertures has flexible fingers 74 which hold the pellet or pellets 77 within the magazine until expelled therefrom by the plunger 20. The front plate 64 also contains locking posts 70, the function of which is described below.

The magazine 66 includes a plurality of pellet cylinders 76 of which there are tenon the magazine disclosed. Additionally the magazine 66 contains forward facing bores 78 corresponding to the locking posts 70 of the front plate 64, and slightly larger rearward facing bores 80 connected to the forward facing bores 78 and corresponding to the locking holes 72 of the rear plate 62 to be described.

The rear plate 62 includes apertures 86 which correspond to the magazine cylinders 76,. Each of the apertures 86 has flexible fingers 84 which hold the pellet or pellets 77 within the magazine 66 until expelled therefrom by the plunger 20. The rear plate 62 also contains locking holes 72 which are sized to fit within the rearward facing bores 80 of the magazine 66. The locking posts 70 of the front plate 64 pass through the forward facing bores 78 of the magazine 66, snapping in to the locking holes 72, thus creating a single sealed part, the strip cartridge 60, which cannot be easily or unobtrusively tampered with.

The rear plate 62 also contains detent strip 68. This strip 68 provides the positioning stops for the detent spring 36 of the strip cartridge adapter 30. FIGS. 4C and 5A show a detent strip 68 of sequential valleys and peaks which when aligned with the detent spring 36 provide for proper alignment of the magazine cylinders 76 with the strip cartridge adapter bore 33 and plunger guide 44. While this provides the preferred indexing and detent means, other indexing and detent means are possible within the scope of the invention.

OPERATION OF CARTRIDGE IMPLANT GUN

To replace the cylinder-type cartridge holder 15 with the strip cartridge adapter 30 the operator places the handgun-type implanter 10 on a flat surface, as shown in FIGS. 6A, 6B, 6C, and 6D with the bottom of the grip portion 12 towards him and the back of the grip portion 12 to his right. He then removes the four screws 58 A. B, C, and D holding the body portion 11 together and, careful not to disturb the internal trigger and plunger mechanism 20-26, lifts off the half of the body portion 11 facing up. He then slides out the cylinder-type cartridge holder 15 and inserts the strip cartridge adpater 30, which fits and is held in place in exactly the same manner. Making sure the trigger and plunge mechanism 20-26 has not been disturbed, he then recloses the gun 10 and reinserts the four screws 58A, B, C, and D. The cylinder-type cartridge holder 15 can be reattached, if use of cylinder-type cartridges 14 is desired, by reversing the above process.

An important advantage with the strip cartridge adapter 30 is, once it has been installed on the implant gun 10 but before the four screws 58 A, B, C, and D which hold the body portion 11 together have been fully tightened, it can be rotated 360° about its axis (defined by the plunger guide 44) to allow positing of the strip cartridge receiving cavity 42 (and therefore the strip cartridge 60) into any desired position. This enables the operator to position the strip cartridge 60 to the angle that is most convenient.

To operate the cartridge implant gun 10 with the adapter 30, the operator selects a strip cartridge 60 containing the proper pellets 77 for the animals to be treated. A major advantage of this invention is that the operator may rapidly change the strip cartridges 60 if different animals are to be treated with different pellets 77.

The operator then inserts the strip cartridge 60 into the receiving cavity 42 on the strip cartridge adaptor 30. A slight pressure will be required to snap the detent strip 68 into the proper position against the detent spring 36. Once snapped into place the magazine cylinder 76 will be en register with the plunger 20 and the bore or pellet conveying conduit 33 in front of the strip cartridge 60. The operator may visually ascertain that the cylinder 76 contains a pellet or pellets 77 by viewing that cylinder 76 through the view port 40 in the top of the strip cartridge adaptor 30.

The cartridge implant gun 10 and the strip cartridge 60 disclosed in this application have the further advantage of allowing pellets 77 of varying sizes and numbers to be used with the same gun 10. The cylinder 76 as disclosed will ordinarily accommodate from one to three cylindrical pellets 77 but can accommodate other shapes such as spherical pellets. Likewise, the cylinder 76 will accommodate a single smaller pellet thus affording considerable flexibility in use.

Numerous characteristics and advantages of our invention have been set forth in the foregoing description, together with details of the structure and function of the invention, and the novel features thereof are pointed out in the appended claims. The disclosure, however, is illustrative only, and changes may be made in detail, especially in matters of shape, size and arrangement of parts, within the principle of the invention, to the full extent indicated by the broad general meaning of the terms in which the appended claims are expressed.

I claim:

1. A strip cartridge adapter for converting a handgun-type implanter that uses a cylinder-type cartridge to a handgun-type implanter that uses a strip cartridge, said strip cartridge adapter comprising;
   (1) an attachment post providing means for attachment of said adapter to said handgun-type implanter.
   (2) an L-shaped strip cartridge receiving cavity formed in said adapter for slidably receiving therein an L-shaped strip cartridge having a plurality of linearly spaced pellet cylinders,
   (3) means for positioning said L-shaped strip cartridge within said cartridge receiving cavity,
   (4) means defining a pellet conveying conduit in alignment with a pellet cylinder when positioned within said cartridge receiving cavity; and
   (5) a view port for visual inspection of said pellet cylinder, 2. The strip cartridge adapter of claim 1 wherein said means for positioning said L-shaped strip cartridge within said cartridge receiving cavity comprises a positioning detent spring, 3. In combination, a strip cartridge adapter for converting a handgun implanter that uses a cylinder-type cartridge to a handgun implanter that uses a strip cartridge and cartridges therefor, said strip cartridge adapter comprising;
   (1) an attachment post providing means for attachment of said adapter to said handgun-type implanter,
   (2) an L-shaped strip cartridge receiving cavity formed in said adapter for slidably receiving therein an L-shaped strip cartridge having a plurality of linearly spaced pellet cylinders,
   (3) means for positioning said L-shaped strip cartridge within said cartridge receiving cavity,
   (4) means defining a pellet conveying conduit in alignment with a pellet cylinder when positioned within said cartridge receiving cavity;
   (5) view port for visual inspection of said pellet cylinder; and an L-shaped strip cartridge sized to slidably fit within the cartridge receiving cavity of the strip cartridge adapter.

4. The combination of claim 3 wherein said strip cartridge comprises
   a plurality of linearly spaced pellet cylinders, each pellet cylinder having a first end, a second end coaxial therewith, and flexible pellet restraining means at the first end and the second end;
   a plurality of indents, one indent associated with each pellet cylinder and cooperating with said cartridge adapter positioning means to cause coaxial alignment of the associated pellet cylinder with said conduit when said positioning means is within an indent.

* * * * *

UNITED STATES PATENT AND TRADEMARK OFFICE
CERTIFICATE OF CORRECTION

PATENT NO. : 5,135,493

DATED : August 4, 1992

INVENTOR(S) : Mark Peschke

It is certified that error appears in the above-identified patent and that said Letters Patent is hereby corrected as shown below:

```
Column 1, line 20, "implate" should read --implant--.
Column 1, line 28, "receive" should read --receiver--.
Column 1, line 41, "describe" should read --described--.
Col. 1, line 46, "framer" should read --farmer--.
Column 2, line 7, "with" should read --which--.
Column 2, line 14, "thereto" should read --hereto--.
Column 3, line 62, "tenon" should read --ten on--.
Column 4, line 35, "adpater" should read --adapter--.
Column 4, line 48, "positing" should read --positioning--.
Col. 4, line 65, "en" should read --in--.
```

Signed and Sealed this

Twenty-fourth Day of August, 1993

*Attest:*

BRUCE LEHMAN

*Attesting Officer*  *Commissioner of Patents and Trademarks*